(12) United States Patent
Gharib et al.

(10) Patent No.: US 6,580,503 B2
(45) Date of Patent: Jun. 17, 2003

(54) PARTICLE SIZING AND CONCENTRATION SENSOR USING A HOLLOW SHAPED BEAM

(75) Inventors: Morteza Gharib, San Marino, CA (US); Dominique Fourguette, LA, CA (US); Frederic Taugwalder, Altadena, CA (US); Daniel W. Wilson, Montrose, CA (US); Darius Modarress, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/006,932

(22) Filed: Dec. 4, 2001

(65) Prior Publication Data

US 2002/0113963 A1 Aug. 22, 2002

Related U.S. Application Data

(60) Provisional application No. 60/251,353, filed on Dec. 4, 2000.

(51) Int. Cl.[7] .................... G01N 15/02; G01N 21/00
(52) U.S. Cl. ............................... 356/336; 356/339
(58) Field of Search .................. 356/335, 336, 356/337, 338, 341, 339, 343, 237.1, 237.2, 237.3

(56) References Cited

U.S. PATENT DOCUMENTS 4,871,257 A * 10/1989 Suzuki et al. ............ 356/237.5

* cited by examiner

Primary Examiner—Michael P. Stafira
(74) Attorney, Agent, or Firm—Fish & Richardson P.C.

(57) ABSTRACT

An optical particle detection system produces an optical beam which is scattered by particles in a probe volume area. The particles may scatter the beam to the detector. The optical beam is a hollow shaped beam which may be circular/doughnut shaped, or made be of any other hollow shape. The particle passes across the beam, and those particles which pass through the center of the beam are detected as being desired particles to detect. This system may be used to detect particle concentration, and size. In addition, by producing an asymmetric beam, particle direction can also be detected.

59 Claims, 3 Drawing Sheets

TIME

TIME

PARTICLE SIZING AND CONCENTRATION SENSOR USING A HOLLOW SHAPED BEAM

CROSS-REFERENCE TO RELATED APPLICATIONS

The present application claims priority from provisional application No. 60/251,353 filed Dec. 4, 2000.

STATEMENT AS TO FEDERALLY-SPONSORED RESEARCH

The U.S. Government has certain rights in this invention pursuant to Grant No. N66001-99-1-8902 awarded by Office of Naval Research.

BACKGROUND

Optical techniques for particle characterization are known. A laser based particle characterization technique is known. The optical techniques may be used to measure the size of particles, and may also be used to measure the concentration of these particles in a two-phase medium. The term 'particles' may be used to refer to any second phase object within a first phase, and may include particles of matter, bubbles or droplets.

One of these techniques uses the so-called IMAX technique which has been described in "Nonintrusive Optical Single-Particle Counter For Measuring The Size And Velocity Of Droplets In A Spray" Applied Optics, Volume 23 No. 23, by Hess. In summary, the IMAX technique uses two laser beams. A smaller-diameter laser beam is used at the measurement location as a pointer beam. A larger diameter laser beam is used at the measurement location as a particle sizing beam. The size of a particle, which passes through the measurement location, may be inferred from the intensity of the scattered light from the particle sizing laser beams based on Mie scattering theory. This requires knowledge of the intensity of the laser at the location where the particle crosses the "particle sizing" laser beam. The lasers have a Gaussian shape and therefore the intensity of the laser is a function of the trajectory of the particle relative to the particle sizing laser.

The pointer laser may decrease the uncertainty. Light which is scattered from the pointer laser is collected. This is used as evidence of the proper trajectory of the particle relative to the particle sizing laser. The pointer layer may also be used to verify that the particle is passing through the flat region of the particle sizing laser. This may reduce or eliminate uncertainty due to the Gaussian shape of the laser.

Particle concentration may be determined from the knowledge of the diameter of the pointer laser, and the velocity of the flow at the measurement location. However, there is still uncertainty in this technique.

Other techniques of determining particle concentration using optical techniques are known. These techniques may use the concept of Mie optical scattering to determine the concentration of particles.

SUMMARY

The present application teaches detecting particle concentration using a special hollow shaped optical beam. In an embodiment, a detection may be made of whether the particle is passing through a specified location within the hollow shape. By detecting the particle beam passing only through this specified location, it becomes possible to even further reduce the uncertainty.

BRIEF DESCRIPTION OF THE DRAWINGS

These and other aspects will now be described in detail with reference to the accompanying drawings, wherein.

DETAILED DESCRIPTION

According to the present invention, a particle sizing beam is formed in the shape of a hollow shaped beam. This beam may be formed using a diffractive optical element. In one embodiment, the beam may be circular in outer and inner cross-section, i.e. in the shape of a doughnut. Other shapes may also be used. An embodiment disclosed herein uses a shape which is hollow but has an irregular inner and outer shape, with flat portions defined on the outer perimeter.

A probe volume is defined as the inside portion of hollow shape. In this embodiment, specified measurements can be used to ensure that the particle goes through a specified portion within that hollow shape. Hence, this may define a well-defined probe volume.

Figure 8:
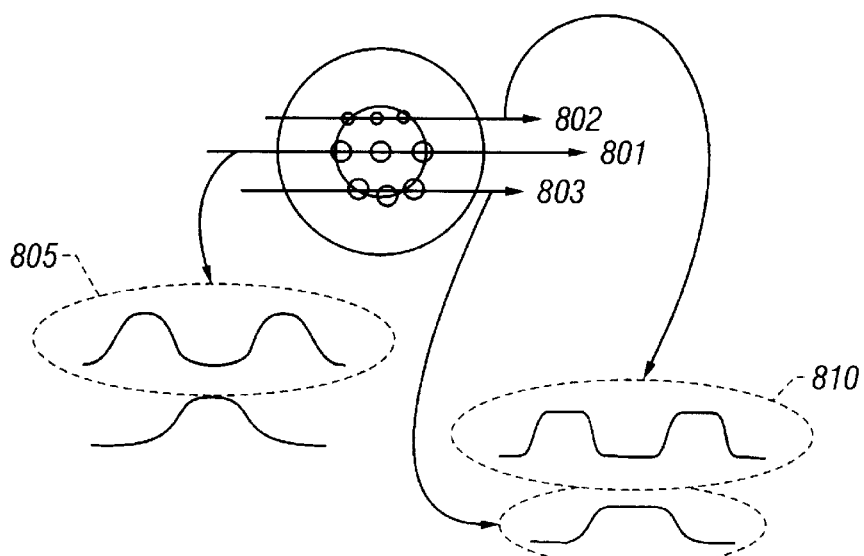
FIG. 8 shows detection of particles passing through the desired area of probe volume.

As disclosed herein, the particle may pass through the hollow shape in a number of different ways. FIG. 8 shows how the particle may pass through a first path 801 which is through the center of the probe volume. This may be considered as the ideal path for the particle, through the center of the hollow beam shape. Passage of the beam through the illuminated portions leads to maxima in the received signal, shown as 805. The signal returns to its baseline state in between the illuminated portions. The particle may also pass through an edge of the probe volume shown as 802. A particle having this trajectory may have a similar envelope shown as the trace 810. When the particle passes to close to the periphery, as shown by 803, there is actually no location where the beam returns to its zero state. The trace 815 shows the particle passing through that path.

Figure 1:
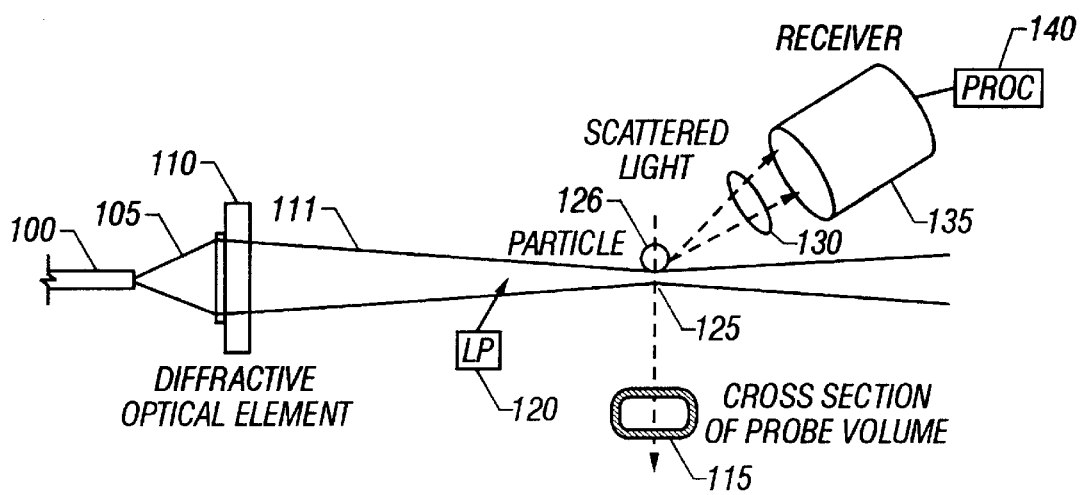
FIG. 1 shows a basic system showing a first embodiment of the particle sizing system for large particles.

The basic technique is shown in FIG. 1. In an embodiment shown in FIG. 1, the particles being detected are larger than 5 um. In this embodiment, therefore, the sensor may operate using only a single laser beam. The optical source 100 may be a semiconductor laser of any type, or simply a fiber pigtailed to a laser and carrying an optical beam. The beam 105 is emitted from the end of the fiber, and coupled to a diffractive optical element 110. The diffractive optical element produces a special sized beam having a shape shown generally as 115. This shape is created in an area called the "probe volume", which is used for measuring the particles. In this embodiment, the hollow beam may have a shape of 300 microns by 100 microns.

In this embodiment, the dimension of the ring has a length to width ratio of approximately 3 to 1, and a flat topped intensity profile. However, other shapes may be used.

A light detector element 120 may be placed in or adjacent the path of the beam in order to monitor laser light intensity.

This may be used for calibration. In an embodiment, the light detector 120 may be a PIN diode. The calibration may be important, since one aspect of this invention may include counting only particles which pass through the edges and return to a baseline level. The calibration may be used to ensure a consistent baseline for such a system.

The focused location, where the reading is located, may be considered as the measurement location area 125. As the particle passes through the measurement location 125, it may scatter the light. The light is scattered to a collection lens 130 that focuses to a receiver 135. The receiver may be an integrated receiver element, or may be more generally a receiver fiber that couples the light to a remote detector.

Figure 2:
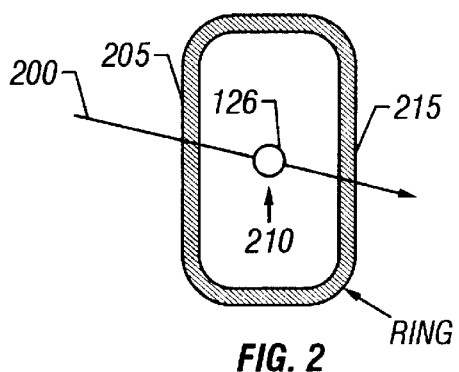
FIG. 2 shows a diagram of the particle passing through a desired area within the hollow shaped beam.
Figure 3:
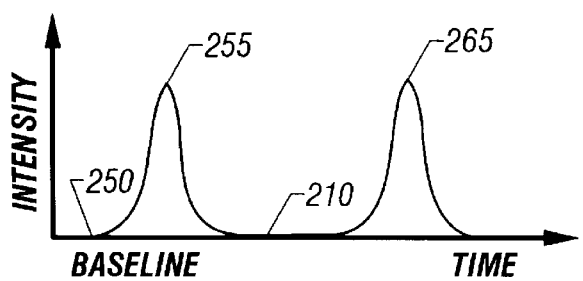
FIG. 3 shows a trace representing the intensity of scattered light from the particle trajectory in FIG. 2.

The output of the receiver is coupled to a processor 140 which operates as conventional to process the information as scattered light, and produce an output indicative of the scattered light. The collection optics 130 is placed off axis relative to the output optical beam 111. For example, the collection optics 130 may be located at an angle between 20 degrees and 45 degrees relative to the optical device 111. The way in which the optics receive the information is illustrated with reference to FIGS. 2 and 3. FIG. 2 represents the particle 126 crossing the probe volume along a particle path 200. As the particle crosses the path, the scattered intensity increases and decreases as shown in FIG. 3. The particle minimum at 250 may be considered the baseline, where there is effectively zero scattering of the light. As the particle passes through the area of the ring 205, a maximum amount of scattering may occur at 255. The particle then enters the hollow center of the beam at 210, during which time the receiver receives substantially zero signal. As the particle passes out the other side of the ring at 215, another maximum is produced at 265.

The size of the particle may be determined from the maximum of the signal intensity, using Mie scattering theory. The velocity of the particle may be inferred from the time of flight between the two lines of the ring 205, 215. Particle velocity may also serve as an accurate indicator of the wind velocity, providing that the particle is small enough to follow the flow motion.

In other embodiments, the aspect ratio of the ring may be changed. Optimization of the ring aspect ratio may be used to vary the line intensity between horizontal and vertical lines. In this way, the sensor may be relatively insensitive to the direction of particle trajectory to about 30 to 45 degrees. This system may also determine both particle size and particle velocity at the same time. The criterion used herein may count or measure only those particles whose signals drop to the baseline between the two maxima. When that happens, it may be inferred that the particle was fully contained inside the ring at shown by 210. Particles which graze the edges of the probe volume generate a signal that does not drop to the baseline between the two maxima.

Figure 4A:
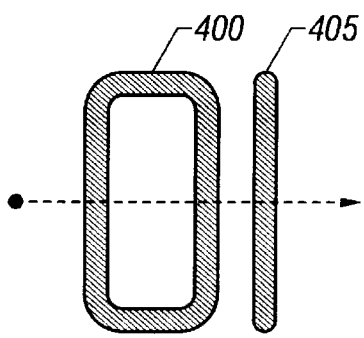
FIGS. 4A and 4B show an asymmetric shape beam and trace from the particle passing through the asymmetric shaped beam.
Figure 4B:
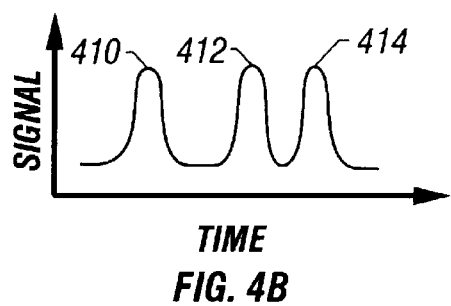

Another embodiment may determine a flow direction by using an asymmetric projection. FIG. 4A shows a first asymmetric projection. In this asymmetric projection, a pattern 400 is provided with a line 405 on one side of the ring. FIG. 4B shows a plot of signal versus time for this device. Note the three peaks at 410, 412, 414. The asymmetry in the pattern allows determination of the direction of flow of the particle. That is, since 412 and 414 are closer to one another than the peaks 410, 412, it can be inferred that the particle is flowing from left to right. The opposite can also be inferred. Moreover, since the pattern 400 is rectangular, the distance between the peaks may be used to infer the angle of particle trajectory.

Figure 5A:
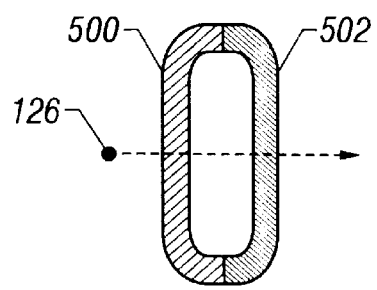
FIGS. 5A and 5B show an asymmetric intensity beam and a trace from a particle passing through that asymmetric intensity beam.
Figure 5B:
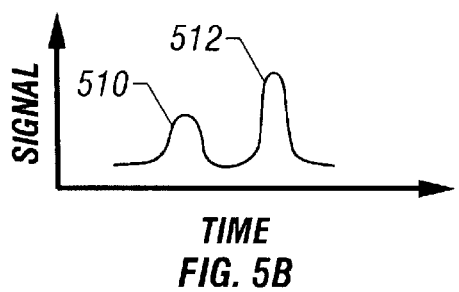

FIGS. 5A and 5B show an alternative embodiment where the pattern is projected with two different intensities within the pattern. The left side of the pattern 500 is projected with a lower intensity than the right side of the pattern 502. As the particle 126 passes through the pattern, it produces a trace shown in FIG. 5B. The peak 510 is produced from the lower intensity portion 500, and is lower than the peak 512 produced from the higher intensity portion 502. Again, since the location of the higher and lower intensity portions are known from the locations of the positions on the trace, the direction of the particle may be inferred.

Another embodiment operates for particles which are smaller than 5 microns. In this embodiment, the particle sizing technique uses the IMAX technique with two laser beams of different wavelengths. In the embodiment, a first laser may be a 532 nm laser, and a second laser 605 may be a 785 nm laser. As discussed above, the dual laser configuration may reduce the uncertainty in particle size caused otherwise by resonance in Mie scattering between the particles.

The two lasers 600, 605 are each coupled to a respective diffractive optical element (DOE) which may be located on the common substrate 610. Each of the diffractive optical elements 612, 614 produce a desired shaped hollow pattern at the probe volume 620. In this embodiment, the laser output is separated from the DOE by about 5 mm shown as dimension 606. The distance between the output of the DOE and the probe volume is about 50 mm shown as dimension 607.

Figure 6:
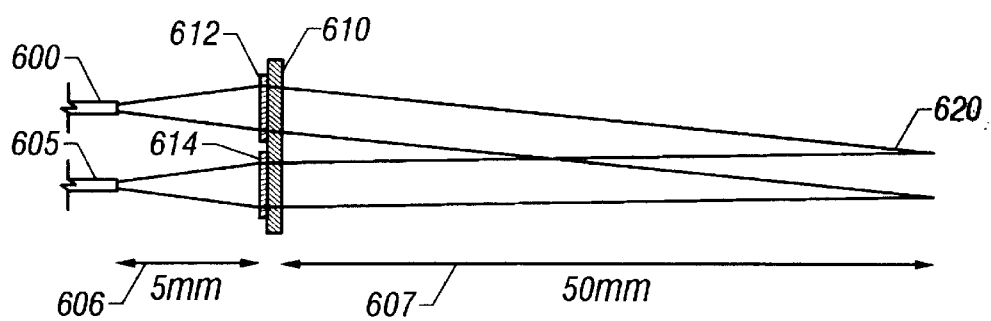
FIG. 6 shows an embodiment for small particles using dual wavelength lasers.
Figure 7:
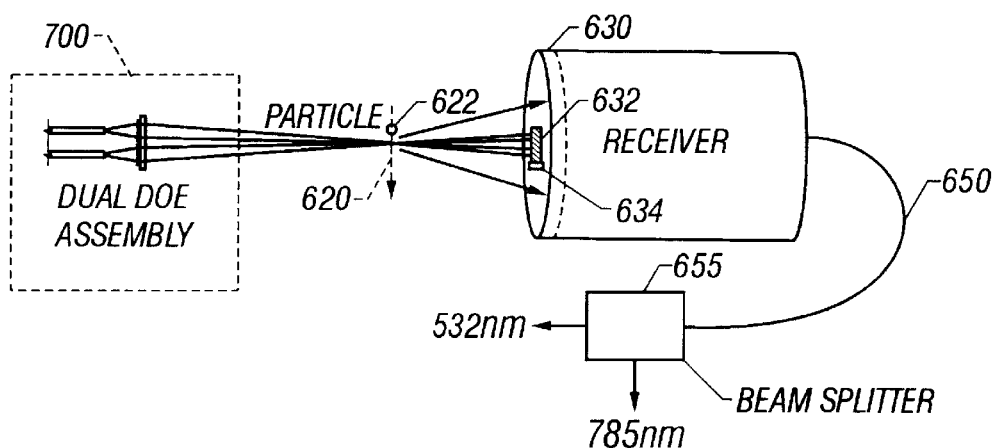
FIG. 7 shows the forward scattering configuration for the small particles.

FIG. 7 shows the collection technique for this system. The dual DOE assembly of FIG. 6 is shown as 700, impinging on the probe volume 620. A particle 622 is shown passing through this probe volume. The collection lens/optics 630 is placed forward of the particle, along the optical axis, in order to take advantage of the strong Mie scattering signal intensity. A mask 632 is placed in the center of the receiver in order to block out the actual laser beam modified by the DOE. The mask may include a PIN diode 634 to monitor the incident laser light intensity. This may be used for calibration. The collecting optics 630 may focus the scattered light into a fiber 650 which may couple the scattered light to a beam splitter 655 that separates the light back into its components of 532 nm and 785 nm. These devices may then use conventional IMAX processing to determine the particle concentration.

Although only a few embodiments have been disclosed in detail above, other modifications are possible. For example, other sources of light and other measuring techniques may be used. In each of these measuring techniques, it may become possible for the system to determine additional information using the same technique as described above.

All such modifications are intended to be encompassed within the following claims, in which:

What is claimed is:

1. A particle measurement system, comprising:
   an optical part, including a holographic element that produces an optical beam along an optical axis, which optical beam has a hollow shape defined by edges and an inside; and
   a scattered light detecting system, detecting light which has been scattered from said optical beam, and producing an output indicative thereof.

2. A particle measurement system, comprising:
   an optical part, including a holographic element that produces an optical beam along an optical axis, which optical beam has a hollow shape defined by edges and an inside; and a scattered light detecting system, detecting light which has been scattered from said optical beam, and producing an output indicative thereof, wherein said optical part includes a laser source and a diffractive optical element.

3. A system as in claim 2, wherein said optical beam is formed of a shape which has sides that are substantially flat.

4. A system as in claim 2, wherein said optical beam is formed of a shape with sides that are substantially round.

5. A system as in claim 2 wherein said scattered light detection system includes an optical receiver which receives light that has been scattered by particles.

6. A system as in claim 5, further comprising a processing element which processes a signal from said optical receiver to determine particle information.

7. A system as in claim 5, wherein said optical receiver includes a lens and an optical receiving element.

8. A system as in claim 2, wherein said laser source includes a diode laser.

9. A system as in claim 2, wherein said laser source includes a laser, with a fiber pigtailed to the laser.

10. A particle measurement system, comprising:
an optical part, including a holographic element that produces an optical beam along an optical axis, which optical beam has a hollow shape defined by edges and an inside; and
a scattered light detecting system, detecting light which has been scattered from said optical beam, and producing an output indicative thereof,
wherein said optical beam is asymmetric.

11. A system as in claim 10, wherein said asymmetric optical beam includes an asymmetric shape which is different on one side than on the other side.

12. A system as in claim 10, wherein said asymmetric optical beam includes an asymmetric intensity distribution.

13. A system as in claim 5, wherein said optical receiver is substantially along said optical axis.

14. A system as in claim 13, further comprising an optical shield which prevents said optical receiver from directly receiving information from the laser beam.

15. A system as in claim 5, wherein said optical receiver is substantially off the axis.

16. A system as in claim 1, wherein said optical part includes a single laser beam.

17. A particle measurement system, comprising:
an optical part, including a holographic element that produces an optical beam along an optical axis, which optical beam has a hollow shape defined by edges and an inside; and
a scattered light detecting system, detecting light which has been scattered from said optical beam, and producing an output indicative thereof,
wherein said optical part includes two separate laser beams which converge at a measuring location.

18. A system as in claim 17, wherein said two separate laser beams have a differing property.

19. A system as in claim 18, wherein said different property have different wavelengths.

20. A system as in claim 1, further comprising a feedback element which detects intensity of the beam.

21. A method, comprising:
using a holographic element to produce a probe volume using a hollow shaped beam; and
receiving scattered light from said hollow shaped beam which has been scattered by particles, and using said scattered light to detect some aspect of the particles.

22. A method as in claim 21, wherein said aspect of said particles which is detected includes concentration.

23. A method, comprising:
using a holographic element to produce a probe volume using a hollow shaped beam;
receiving scattered light from said hollow shaped beam which has been scattered by particles, and using said scattered light to detect some aspect of the particles; and
detecting a first peak and a second peak representing the particles passing from respective sides of the hollow shaped beam.

24. A method as in claim 23, wherein said using comprises determining whether a beam representing an amount of scattered light returns to a baseline level between said first and second peaks.

25. A method as in claim 24, further comprising using information from said beam only when it returns to said baseline level.

26. A method as in claim 21, wherein said aspect of the particles includes particle velocity.

27. A method as in claim 21, wherein said aspect of the particles represents particle moving direction.

28. A method as in claim 27, wherein said hollow shaped beam is an asymmetric hollow shaped beam.

29. A method as in claim 21, wherein said beam has an asymmetric shape.

30. A method as in claim 29, further comprising determining distances between peaks, and determining direction of the particle from said distances between peaks.

31. A method as in claim 28, wherein said asymmetric shape includes a first hollow part, and a second non hollow part.

32. A method as in claim 27, wherein said beam has an asymmetric intensity profile.

33. A method as in claim 32, further comprising determining an intensity of scattered information, and determining a direction of the particle from a distribution and intensity of peaks within said scattered information.

34. A method as in claim 21, wherein said producing comprises producing a single laser beam.

35. A method as in claim 21, wherein said producing comprises producing two laser beams, both directed at said probe volume.

36. A method as in claim 21, wherein said hollow shaped beam has a substantially round in an outer shape.

37. A method as in claim 21, wherein said hollow shaped beam has substantially flat portions on its inner and outer shape.

38. A method as in claim 37, further comprising optimizing an aspect ratio between length and width of said hollow shaped beam.

39. A method as in claim 21, wherein said receiving comprises receiving scattered light on a similar axis to the production of said hollow shaped beam.

40. A method as in claim 21, wherein said receiving comprises receiving scattered light off-axis from the production.

41. A particle sensing system, comprising:
a laser production system;
a diffractive optical element, receiving light from said laser production system, and shaping said light into a hollow shaped beam and directing said hollow shaped beam to a probe volume;
a light receiving part, receiving scattered light from said probe volume, and producing an output signal indicative thereof.

42. A particle sensing system as in claim 41, further comprising a processing element, which processes said output signal to determine information about particles in said probe volume.

43. A particle sensing system as in claim 42, wherein said processing element processes information only from those particles which pass within a specified area within said hollow shaped beam.

44. A particle sensing system as in claim 43, wherein said specified area includes an area within a center of said hollow shaped beam.

45. A particle sensing system as in claim 42, wherein said diffractive optical element produces an asymmetric hollow shaped beam.

46. A particle sensing system as in claim 45, wherein said beam is asymmetric in shape.

47. A particle sensing system as in claim 45, wherein said beam is asymmetric in intensity.

48. A particle sensing system as in claim 45, wherein said processing element uses information from said asymmetric beam to determine particle direction.

49. A particle sensing system as in claim 41, further comprising a calibrating element, which detects intensity of the beam and produces a calibration signal.

50. A particle sensing system, comprising:
 a laser beam;
 an optical shaping element, including a holographic element shaping said laser beam into a hollow shape, and directing said hollow shape along an optical axis to a probe volume;
 a calibration element, monitoring intensity of said hollow shaped laser beam; and
 a scattered light processing element, receiving light which has been scattered by particles in said probe volume, and producing output signals based on only specified ones of said particles which have passed through a specified location in said hollow shaped beam, said specified location beam detected relative to information received by said calibration element.

51. A system as in claim 50, wherein said specified shape is a central portion of said hollow shaped beam, and said central portion is detected based on using intensity information received from said calibration element.

52. A system as in claim 50, wherein said hollow shaped laser beam has at least first and second flat portions.

53. A system as in claim 50, wherein said hollow shaped laser beam has a round outer section.

54. A system as in claim 50, wherein said optical shaping element is a diffractive optical element.

55. A system as in claim 50, wherein said optical shaping element produces an asymmetric beam.

56. A system as in claim 55, wherein said scattered light processing element detects direction of the particles.

57. A system as in claim 55, wherein said asymmetric beam is asymmetrically shaped.

58. A system as in claim 55, wherein said asymmetric beam has an asymmetric intensity profile.

59. A method, comprising:
 using a holographic element projecting a beam at a probe volume, said beam having an asymmetrical shape and having a hollow shape within outer perimeter that is illuminated and an inner part within said outer perimeter that is not illuminated;
 electronically detecting a particle passing through said inner part along a specified path; and
 processing signals from particles which pass through said inner part in said specified way and rejecting signals which do not pass through said specified part in said specified way.

* * * * *